United States Patent
Price et al.

(10) Patent No.: US 10,576,036 B2
(45) Date of Patent: Mar. 3, 2020

(54) TOOTHPASTE AND MOUTH RINSE

(71) Applicant: EWC & Associates, LLC, Phoenix, AZ (US)

(72) Inventors: Ginger Price, Phoenix, AZ (US); Martin Giniger, New York, NY (US)

(73) Assignee: EWC & Associates, LLC, Phoenix, AZ (US)

( * ) Notice: Subject to any disclaimer, the term of this patent is extended or adjusted under 35 U.S.C. 154(b) by 0 days.

(21) Appl. No.: 16/205,532

(22) Filed: Nov. 30, 2018

(65) Prior Publication Data

US 2019/0167558 A1    Jun. 6, 2019

Related U.S. Application Data

(63) Continuation of application No. 15/207,406, filed on Jul. 11, 2016, now Pat. No. 10,149,815.

(60) Provisional application No. 62/190,298, filed on Jul. 9, 2015.

(51) Int. Cl.

| | | |
|---|---|---|
| *A61K 8/92* | (2006.01) | |
| *A61Q 11/00* | (2006.01) | |
| *A61K 8/42* | (2006.01) | |
| *A61K 8/27* | (2006.01) | |
| *A61K 8/34* | (2006.01) | |
| *A61K 8/29* | (2006.01) | |
| *A61K 8/25* | (2006.01) | |
| *A61K 8/46* | (2006.01) | |
| *A61K 8/97* | (2017.01) | |

(52) U.S. Cl.
CPC .............. *A61K 8/922* (2013.01); *A61K 8/25* (2013.01); *A61K 8/27* (2013.01); *A61K 8/29* (2013.01); *A61K 8/345* (2013.01); *A61K 8/42* (2013.01); *A61K 8/463* (2013.01); *A61K 8/97* (2013.01); *A61Q 11/00* (2013.01)

(58) Field of Classification Search
None
See application file for complete search history.

(56) References Cited

U.S. PATENT DOCUMENTS

| | | | |
|---|---|---|---|
| 5,906,811 A * | 5/1999 | Hersh | A61K 8/02 424/49 |
| 9,044,466 B2 * | 6/2015 | Cohen | A61K 31/435 |
| 9,114,097 B1 * | 8/2015 | Aminpour | A61K 8/97 |
| 2012/0244087 A1 * | 9/2012 | Trivedi | A23G 4/068 424/48 |
| 2015/0147368 A1 * | 5/2015 | Goode | A61K 8/25 424/401 |

* cited by examiner

*Primary Examiner* — Nannette Holloman
(74) *Attorney, Agent, or Firm* — David G. Rosenbaum; J. Peter Paredes; Rosenbaum IP, P.C.

(57) ABSTRACT

Formulations for oral care products that incorporate coconut oil for effectively removing bacteria from the mouth and methods for making these products are disclosed herein.

12 Claims, 2 Drawing Sheets

FIG. 1:

Holistic and Healthy Coconut Alcohol Free Mouth Rinse

|  | % |
|---|---|
| Phase A | |
| Alkaline Water | 40.375 |
| Pure Coconut Flavor Oil Extract | 12.626 |
| Phase B | |
| Alkaline Water | 12.178 |
| Sodium Lauryl Sarcosinate | 0.022 |
| Phase C | |
| Zinc Chloride | 0.7 |
| 30% Xylitol Solution | 10 |
| Phase D | |
| Glycerin | 10 |
| Aloe Barbadensis Leaf Juice | 4 |
| Phase E | |
| Sodium Benzoate | 0.099 |
| Phase F | |
| De-ionized Water | 9.7 |
| Natural Mint Flavor Extract | 0.3 |

FIG. 2:

Holistic and Healthy Coconut Oil Toothpaste

| FORMULA | % |
|---|---|
| Alkaline Water | 35.5 |
| Coconut Oil | 27.75 |
| Hydrated Sylica Sident 9 | 15.4 |
| Hydrated Silica Sident 22s | 2.8 |
| Glycerin | 10.5 |
| Xylitol | 4 |
| Irish Moss | 1.4 |
| Sodium Coco Sulphate | 0.7 |
| Organic Aloe Barbadensis Leaf Juio | 0.7 |
| Titanium Dioxide | 0.65 |
| Flavor | 0.6 |

TOOTHPASTE AND MOUTH RINSE

CROSS-REFERENCE TO RELATED APPLICATIONS

The present application claims priority from and is a continuation of U.S. patent application Ser. No. 15/207,406, filed Jul. 11, 2016, which issued as U.S. Pat. No. 10,149,815 on Dec. 11, 2018; which claims priority from U.S. Provisional Application Ser. No. 62/190,298, filed Jul. 9, 2015, each herein incorporated by reference in their entirety.

BACKGROUND

Oral inflammation and the bacteria that causes it are the enemy of good and stable oral health. Preventing oral inflammation saves a person from not only pain and discomfort but also expense and trouble of doctor visits and treatments. Coconut oil has been used in oral health practices to aid in removal of bacteria from the mouth. The use of coconut oil has been proven effective in this line of use, and therefore, has been incorporated into oral health practices. In addition, the use of coconut oil helps people maintain good oral and dental health without using fluoride.

It is thus desirous to have oral care products that uses coconut oil in order to effectively remove the bacterial that causes oral inflammation.

SUMMARY OF THE INVENTION

The structure, overall operation and technical characteristics of the present invention will become apparent with the detailed description of preferred embodiments and the illustration of the related figures as follows.

This invention is embodied in formulations for oral care products including a toothpaste and a mouth rinse that incorporate coconut oil and its helpful properties and methods for making such products. The high content of coconut oil in these products distinguishes them from the prior art and accentuates the useful properties of the products.

One object of this invention is to provide formulations for oral care products that accentuate the useful properties of coconut oil in removing the bacteria that cause oral inflammation.

Another object of this invention is to provide methods for making such oral care products.

The methods, systems, and apparatuses are set forth in part in the description which follows, and in part will be obvious from the description, or can be learned by practice of the methods, apparatuses, and systems. The advantages of the methods, apparatuses, and systems will be realized and attained by means of the elements and combinations particularly pointed out in the appended claims. It is to be understood that both the foregoing general description and the following detailed description are exemplary and explanatory only and are not restrictive of the methods, apparatuses, and systems, as claimed.

BRIEF DESCRIPTION OF THE FIGURES

In the accompanying figures, like elements are identified by like reference numerals among the several preferred embodiments of the present invention.

FIG. 1 is a table showing a preferred formulation of a mouth rinse having coconut oil.

FIG. 2 is a table showing a preferred formulation of a toothpaste having coconut oil.

DETAILED DESCRIPTION OF THE INVENTION

The foregoing and other features and advantages of the invention are apparent from the following detailed description of exemplary embodiments, read in conjunction with the accompanying figures. The detailed description and figures are merely illustrative of the invention rather than limiting, the scope of the invention being defined by the appended claims and equivalents thereof.

Embodiments of the invention will now be described with reference to the Figures, wherein like numerals reflect like elements throughout. The terminology used in the description presented herein is not intended to be interpreted in any limited or restrictive way, simply because it is being utilized in conjunction with detailed description of certain specific embodiments of the invention. Furthermore, embodiments of the invention may include several novel features, no single one of which is solely responsible for its desirable attributes or which is essential to practicing the invention described herein. The words proximal and distal are applied herein to denote specific ends of components of the instrument described herein. A proximal end refers to the end of an instrument nearer to an operator of the instrument when the instrument is being used. A distal end refers to the end of a component further from the operator and extending towards the surgical area of a patient and/or the implant.

The use of the terms "a" and "an" and "the" and similar referents in the context of describing the invention are to be construed to cover both the singular and the plural, unless otherwise indicated herein or clearly contradicted by context. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

Recitation of ranges of values herein are merely intended to serve as a shorthand method of referring individually to each separate value falling within the range, unless otherwise indicated herein, and each separate value is incorporated into the specification as if it were individually recited herein. The word "about," when accompanying a numerical value, is to be construed as indicating a deviation of up to and inclusive of 10% from the stated numerical value. The use of any and all examples, or exemplary language ("e.g." or "such as") provided herein, is intended merely to better illuminate the invention and does not pose a limitation on the scope of the invention unless otherwise claimed. No language in the specification should be construed as indicating any nonclaimed element as essential to the practice of the invention.

References to "one embodiment," "an embodiment," "example embodiment," "various embodiments," etc., may indicate that the embodiment(s) of the invention so described may include a particular feature, structure, or characteristic, but not every embodiment necessarily includes the particular feature, structure, or characteristic. Further, repeated use of the phrase "in one embodiment," or "in an exemplary embodiment," do not necessarily refer to the same embodiment, although they may.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, and biochemical arts. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

In one embodiment, a mouth rinse contains alkaline water, coconut flavor oil extract, sodium lauryl sarcosinate, zinc chloride, 30% xylitol solution, glycerin, aloe barbadensis leaf juice, and optionally, sodium benzoate, de-ionized water, and mint flavor extract. A preferred toothpaste contains alkaline water, coconut oil, hydrated sylica sident 9, hydrated silica sident 22s, glycerin, xylitol, Irish moss, sodium coco sulphate, aloe babadensis leaf juice, titanium dioxide, and flavor. The percentage of the coconut oil content in the preferred products is in the range of 20%-80%, but most preferably 40%-60%.

FIG. 1 shows the details of a preferred formulation of the coconut alcohol free mouth rinse. The preferred mouth rinse is prepared in 6 separate phases and then all 6 phases are mixed together in order. Phase A contains 40.375% Alkaline Water and 12.626% Pure Coconut Flavor Oil Extract. Phase B contains 12.178%.

Alkaline Water and 0.022% Sodium Lauryl Sarcosinate. Phase C contains 0.7% Zinc Chloride and 10% 30% Xylitol Solution. Phase D contains 10% Glycerin and 4% Aloe Barbadensis Leaf Juice. Phase E contains 0.099% of Sodium Benzoate. Phase F contains 9.7% De-ionized Water and 0.3% Natural Mint Flavor Extract.

While this is the preferred embodiment of the mouth rinse mixture, the percentages of ingredients can be varied. In particular, the coconut oil content of the mixture is in the range of 20%-80%, but most preferably 40%-60%. Phases E and F may be omitted.

The preferred instructions for mixing the mouth rinse comprise first, pre-mixing a 30% Xylitol Solution. Second, Phase A, Phase B, Phase C, Phase D, and Phase F are each mixed separately. They are mixed until the solution is clear. Finally, Phases A, B, C, D, E, and F are combined in order. Mix at slow speed until homogeneous. The Xylitol solution, mint flavor, and coconut flavor can be adjusted to taste.

FIG. 2 shows the details of a preferred formulation of the coconut oil toothpaste. The toothpaste contains 35.5% Alkaline Water, 27.75% Coconut Oil, 15.4% Hydrated Sylica Sident 9, 2.8% Hydrated Silica Sident 22s, 10.5% Glycerin, 4% Xylitol, 1.4% Irish Moss, 0.7% Sodium Coco Sulphate, 0.7% Organic Aloe Barbadensis Leaf Juice, 0.65% Titanium Dioxide, and 0.6% Flavor.

While this is the preferred embodiment of the toothpaste mixture, the percentages of ingredients can be varied. In particular, the coconut oil content is in the range of 20%-80%, but most preferably 40%-60%.

The preferred instructions for mixing the toothpaste comprise, first, to a clean sanitized vessel with sweep agitation and homogenization add Water, Sodium Coco Sulphate, Xylitol, Glycerin and Titanium Dioxide. Second, mix 5 minutes between ingredient additions under sweeps (16±2 RPM). Third, once all ingredients have been added at 16±2 RPM, continue mixing for 30 minutes under vacuum.

Next, in a separate vessel blend the Irish Moss and Silica. Use ⅓ of Sident 9 and ⅓ of Irish Moss and mix by hand. Repeat 2 more times in the same container, until all Sident 9 and Irish Moss are mixed. Add this first ⅓ of the pre-mix to the main vessel with homogenizer ON under vacuum at 16±2 RPM. Repeat 2 more times until all of the pre-mix has been added. Mix for 10 more minutes. Add Sident 22s to the main vessel and continue mixing under vacuum.

Once the main vessel is uniformly mixed, add the Aloe Juice and the Flavor.

Continue to mix (16±2 RPM) under vacuum with sweeps for 30 minutes. Once everything is homogenous and looking like finished toothpaste, add Coconut Oil at 16±2 RPM with NO Homogenizer under vacuum. QC to analyze and taste. Package to portable container for filling.

Additionally, a preferred embodiment of the toothpaste with at least 40% of natural coconut oil is shown to have a strong antimicrobial effect, as well as satisfactory whitening and breath freshening effects. A clinical study of this preferred embodiment shows that the embodiment killed 99% of all microorganisms tested. In contrast, the placebo and the control toothpaste (the Crest™ anti-cavity toothpaste) did not show antimicrobial activity against any of the 23 tested microorganisms. Furthermore, this embodiment was the only formulation in the study that had activity against Gram-negative bacteria (*Psudomonas aeruginosa*) which is a critical bacterial species that contributes to periodontal disease. Therefore, the preferred toothpaste can be used to effectively prevent oral inflammation caused by bacteria.

The aforementioned embodiments are preferably used 2 times daily for maximum benefits. For the preferred toothpastes, it is recommended that a user uses them with a soft bristle toothbrush and brush at least one minute. For the preferred mouth rinse, it is recommended that a user swishes vigorously 10 ml between teeth for at least one minute and then spits out.

While the invention has been described in connection with various embodiments, it will be understood that the invention is capable of further modifications. This application is intended to cover any variations, uses or adaptations of the invention following, in general, the principles of the invention, and including such departures from the present disclosure as, within the known and customary practice within the art to which the invention pertains.

What is claimed is:

1. A mouth rinse comprising:
   a. Alkaline water, wherein a percentage of alkaline water is between about 35.5% and about 52.553%;
   b. Coconut flavor oil extract, wherein a percentage of the coconut flavor oil extract is between about 20% to about 80%;
   c. Sodium lauryl sarcosinate, wherein a percentage of the sodium lauryl sarcosinate is about 0.022%;
   d. Zinc chloride, wherein a percentage of the zinc chloride is about 0.7%;
   e. 30% xylitol solution, wherein a percentage of 30% xylitol solution is about 10%; and
   f. Glycerin, wherein a percentage of glycerin is about 10%.

2. The mouth rinse according to claim 1 further comprising sodium benzoate.

3. The mouth rinse according to claim 1, further comprising Aloe barbadensis leaf juice, wherein a percentage of Aloe barbadensis leaf juice is between about 0.7% and about 4%.

4. The mouth rinse according to claim 1, further comprising a flavor extract.

5. The mouth rinse according to claim 1 further comprises:
   a. Sodium benzoate;
   b. De-ionized water; and
   c. Mint flavor extract.

6. The mouth rinse according to claim 5 wherein:
   h. a percentage of the sodium benzonate is about 0.099%,
   i. a percentage of the de-ionized water is about 9.7%, and
   J. a percentage of the mint flavor extract is about 0.3%.

7. A method for creating a mouth rinse comprising the steps of:
   a. Mixing a 30% xylitol solution;
   b. Mixing alkaline water and pure coconut flavor oil extract into step A, wherein a percentage of the alkaline water is about 40.375% and a percentage of coconut flavor oil extract is about 12.626%;
   c. Mixing alkaline water and sodium lauryl sarcosinate into step B, wherein a percentage of the sodium lauryl sarcosinate is about 0.022%;
   d. Mixing zinc chloride and the 30% xylitol solution into step C, wherein a percentage of the 30% xyloitol solution is about 10% and a percentage of the zinc chloride is about 0.7%;
   e. Mixing glycerin and Aloe barbadensis leaf juice into step D, wherein a percentage of the glycerin is about 10% and a percentage of the Aloe barbadensis leaf juice is about 4%; and
   f. Combining steps A, B, C, D, and flavoring in order and mixing until homogeneous.

8. The method of claim 7 wherein:
   a. the flavoring further comprises de-ionized water and mint flavor extract,
   b. a percentage of the de-ionized water is about 9.7%, and
   c. a percentage of the mint flavor extract is about 0.3%.

9. The method of claim 8 further comprises the step of mixing the mouth rinse with sodium benzoate, wherein a percentage of the sodium benzoate is about 0.099%.

10. A toothpaste comprising:
    a. Alkaline water at a percentage of about 35.5%;
    b. Coconut oil at a percentage between about 20%-80%;
    c. Thickening silica at a percentage of about 15.4%;
    d. Abrasive silica at a percentage of about 2.8%;
    e. Glycerin at a percentage of about 10.5%;
    f. Xylitol at a percentage of about 4%;
    h. Sodium coco sulphate at a percentage of about 0.7%;
    i. Aloe babadensis leaf juice at a percentage of about 0.7%;
    J. Titanium dioxide at a percentage of about 0.65%; and
    k. Flavor at a percentage of about 0.6%.

11. The toothpaste of claim 10, wherein the coconut oil is at a percentage of about 40%.

12. The toothpaste of claim 10, further comprising Irish moss at a percentage of about 1.4%.

* * * * *